United States Patent [19]

Belcher et al.

[11] 3,981,585

[45] Sept. 21, 1976

[54] MOLECULAR CAVITY ANALYSIS-FILTER CAVITY

[75] Inventors: Ronald Belcher; Alan Townshend; Stanley L. Bogdanski, all of Birmingham, England

[73] Assignee: Anacon, Inc., Ashland, Mass.

[22] Filed: Feb. 3, 1975

[21] Appl. No.: 546,197

Related U.S. Application Data

[63] Continuation-in-part of Ser. No. 389,587, Aug. 20, 1973, Pat. No. 3,871,768.

[52] U.S. Cl. .................................. 356/87; 356/36; 356/187; 356/244
[51] Int. Cl.² ............................................. G01J 3/30
[58] Field of Search .............. 356/36, 87, 187, 244, 356/246

[56] References Cited
UNITED STATES PATENTS

| | | | |
|---|---|---|---|
| 2,706,928 | 4/1955 | Lee et al. ............................... | 356/87 |
| 3,565,538 | 2/1971 | Kahn et al. ........................ | 356/87 X |
| 3,586,446 | 6/1971 | Findl et al. ........................... | 356/187 |
| 3,708,228 | 2/1973 | Delves .................................. | 356/87 |
| 3,824,016 | 7/1974 | Woodriff et al. ................. | 356/36 X |

OTHER PUBLICATIONS
Belcher et al. *Talanta*, vol. 19, No. 9, Sept. 1972 pp. 1049–1058.

*Primary Examiner*—John K. Corbin
*Assistant Examiner*—F. L. Evans

[57] ABSTRACT

Apparatus is disclosed for pre-treating and spectrally analyzing a sample of matter, including a structure for promoting reaction of an analyte to produce characteristic effects of the analyte measurable by an optical analysis device. The structure defines a sheltered region for containing the analyte, a support surface within the region for supporting a filtering medium, an exposure path for exposing the analyte to an energy source and an optical path leading out of the sheltered region along which radiation characteristic of a property of the analyte proceeds to the optical analysis device.

4 Claims, 6 Drawing Figures

MOLECULAR CAVITY ANALYSIS-FILTER CAVITY

This is a continuation-in-part of our copending application Ser. No. 389,587, filed Aug. 20, 1973, now U.S. Pat. No. 3,871,768, issued Mar. 18, 1975.

BACKGROUND OF THE INVENTION

This invention relates to a structure useful in spectrally analyzing samples of matter.

One of the disadvantages of most known methods of spectral analysis, especially in the case of emission spectroscopy, is that the sample is destroyed almost immediately, so the time available for analysis is very short and, normally, only one element can be investigated at a time. If a broader analysis is required, either several separate analyses are necessary or a technique has to be adopted for continuous introduction of a sample, such as, in flame emission spectroscopy, by aspirating it into a flame. The latter techniques are either not suitable for particular samples or are otherwise unsatisfactory, for example due to overheating, or they are relatively complicated. In any case where more than one element is to be investigated, a relatively large and homogeneous sample is required.

Another disadvantage of the known methods of flame emission spectroscopy for small samples concerns the lack of consistency, uniformity and reproducibility of results. It is often necessary to filter the sample to be analyzed as a preliminary step before introduction into the cavity to concentrate or purify it.

SUMMARY OF THE INVENTION

The present invention provides an apparatus for and method of atomic and molecular spectroscopy which aims at overcoming the said disadvantages; in particular, it enables a broad analysis to be made of a single small sample, and it enables an analysis to be made which is reproducible to an improved degree. The structure promotes interactions between samples of matter or between matter and light which, in many cases, endure for several minutes, thereby enabling a broad analysis to be made. Solvent effects, causing background signals or "noise" can often be eliminated. Further, structures embodying the present invention: enable the user to reduce the number of transfers of the sample to be analyzed, hence smoothing the operating and better insuring reproducible results; enable concentration of large samples to analyzable size; allow the user to quickly and easily change filters for adaptation to a wide variety of analyzable samples; and are simple and inexpensive to manufacture.

In general, the invention features a structure for interaction involving an analyte or reactant, to produce effects characteristic of the analyte, which are measurable by an optical analysis device. The structure is adapted for use with an energy source, i.e. a flame or light source, and defines a sheltered region for sheltering the analyte from the ambient environment, a support surface disposed within the sheltered region for supporting a filter, upon which analyte may be collected either before or after mounting in the sheltered region, an exposure path leading into the sheltered region for exposing volatiles from the analyte to the energy source, and an optical path leading out of the sheltered region along which radiation, dependent upon a characteristic of the analyte, can proceed to the optical analysis device for analysis. In preferred embodiments, the structure includes means to produce a flame and means to expose the structure to the flame to heat analyte on the filter and produce volatiles therefrom, and the exposure path is adapted to admit flame gas into the sheltered region, whereby, under conditions influenced by the structure, flame gas and volatiles from the analyte can mix and interact to produce radiation characteristic of the interaction directed along the optical path. Embodiments of the filter support surface include a filter mounting means comprising a truncated conical surface for receiving an interfitted truncated conical filter and a peripheral surface projecting into the sheltered region from its walls for receiving a disc shaped filter.

For filtrations done directly within the sheltered region, an embodiment of the structure defines a passage communicating between a portion of the sheltered region behind the filter mounting means and exit port to where suction apparatus may be attached.

In still another embodiment of the invention, the sheltered region and the end of the structure housing the exit port are cooperatively constructed such that two or more structures of like design may be interfitted to form a seal, whereby, when a multiplicity of such structures are attached, head to tail, fluid containing a plurality of separable analytes may be filtered through the attached structures and the filters may be chosen to selectively retain and thereby separate the analytes.

The method contemplated by the invention is characterized by the steps of providing an emission promoting structure defining a sheltered region, providing a filtering medium, passing fluid containing reactant through the medium either before or after mounting it within the sheltered region, vaporizing the reactant on the filter within the region, exposing reactant vapor within the region to flame gas, and focusing an optical analysis device upon the interacting gases.

The background of the present invention and structure are described in our U.S. Pat. No. 3,871,768 which is incorporated herein by reference.

DESCRIPTION OF THE PREFERRED EMBODIMENT

Figure 1:
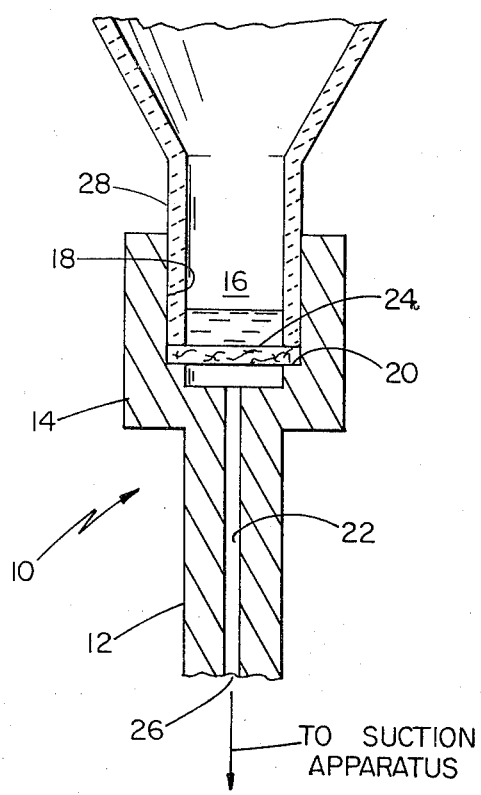
FIG. 1 is a cut away view of a structure embodying the invention assembled for filtration.
Figure 2:
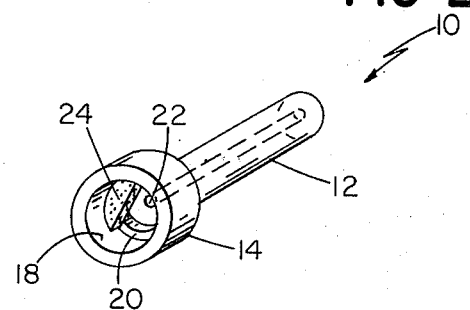
FIG. 2 is a front partially cut away perspective view of the structure of FIG. 1 looking into the cavity.

Referring to FIG. 1, structure 10 comprises a support shaft 12 and head 14. Sheltered region 16 is 8 mm. in diameter and is bounded by cylindrical surface 18 and peripheral filter mounting surface 20, the latter projecting radially inwardly, 8 mm. from the opening of the cavity. Passage 22 extends from the back of sheltered region 16 to an aspirator (not shown).

In operation, a filter 24 is placed inside the sheltered region resting on surface 20 and the structure is held in a vise. When an aspirator is attached to exit port 26, funnel tube 28 is pressed into the cavity (FIG. 1) until its end surface firmly engages filter 24 and prevents any leakage. Fluid containing reactant enters from the funnel tube. The fluid passes through the filter to the aspirator, the reactant remains in filter 24.

Any filter which does not itself exhibit characteristic absorptions or whose optical effect, emission or fluorescence, may be screened out may be used in the apparatus and chosen to suit a particular sample. Controlled porosity stainless steel, sintered quartz or glass, and hasteloy steel fiber filters have been used with success. Since the cavity and filter may be made of materials having different thermal conductivity, reactant sample deposited on the walls of the cavity may volatilize at a different time than sample on the filter due to differentials in the temperature gradient of the respective surfaces. The seal of funnel tube 28 against the filter medium obviates this difficulty, avoiding two emissions (one from each material) by restricting deposit of the reactant to the filter only. On removal of the funnel tube, the filter is frictionally held in place or may be retained by an O-ring suitably placed.

Passage 22 may be used during analysis as an entry port to blow back reactant contained in the filter with an inert gas or as a conduit to introduce oxygen into the cavity, which, in some circumstances, enhances emission by the formation of oxides.

Figure 4:
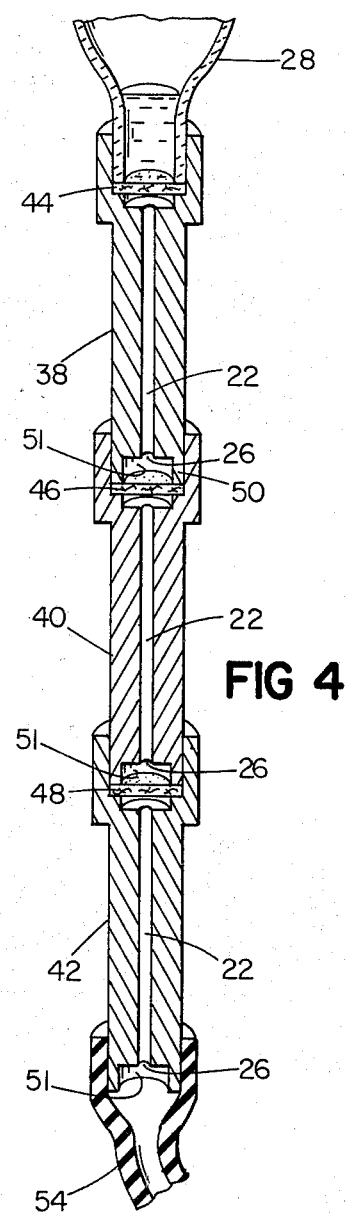
FIG. 4 is a cut away view of a second embodiment of the invention with three structures attached together to form a filter train.

Referring to FIG. 4, three emission promoting structures, 38, 40 and 42 represent a modification of the structure of FIG. 1 which enables the construction of a filter train. When an analysis is required of a fluid containing a mixture of components, filters are chosen which will trap one component but allow the others to pass. For example, in analyzing flue gas, a first filter might be employed to remove particulate matter, a second, impregnated with silver, might be used to trap sulfides, and a third, containing silica gel, might be used to collect sulfur dioxide. A filter 44 is placed in the cavity of a first clamped structure 38, a second filter 46 is placed in a second said structure 40, and the end 50 of the first structure is pressed into the second structure's cavity, sealing upon the filter 46. This attaching process may be repeated to form a train of holders as long as desired, each carrying its selective filter. The end of the last structure (e.g. 42) is connected to the hose 54 of a suction apparatus. The end of each structure is constructed so as to fit within the cavity of an identical structure to form a seal with the filter and has a hollow space 51, enabling exposure of an area of the filter to the sample. When the sample to be analyzed is fed through the funnel tube 28 (or other suitable device) and the suction turned on, fluid is drawn through each filter, exit passage 22, and exit port in turn, resulting in separation of the components of the sample into their respective cavities. Analysis is accomplished by dismantling the filter train, the contents of each structure being detected separately. It will be appreciated that the term "filter" includes means for separation of the components of a sample by either physical or chemical means such as absorption.

Figure 5:
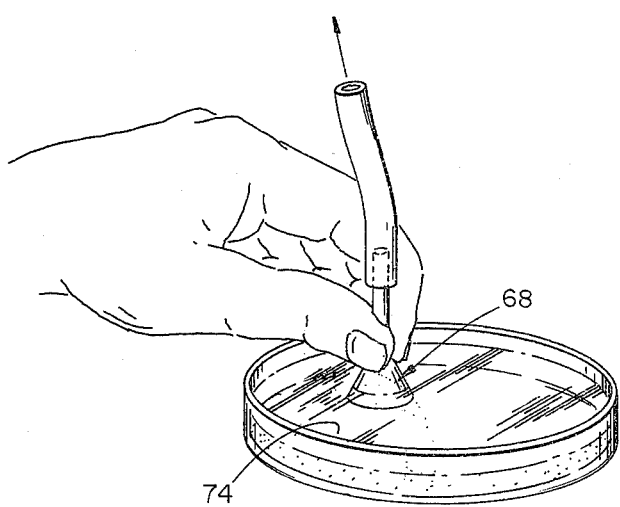
FIG. 5 is a perspective view of the filter of a third embodiment of the invention during collection of analyte.
Figure 6:
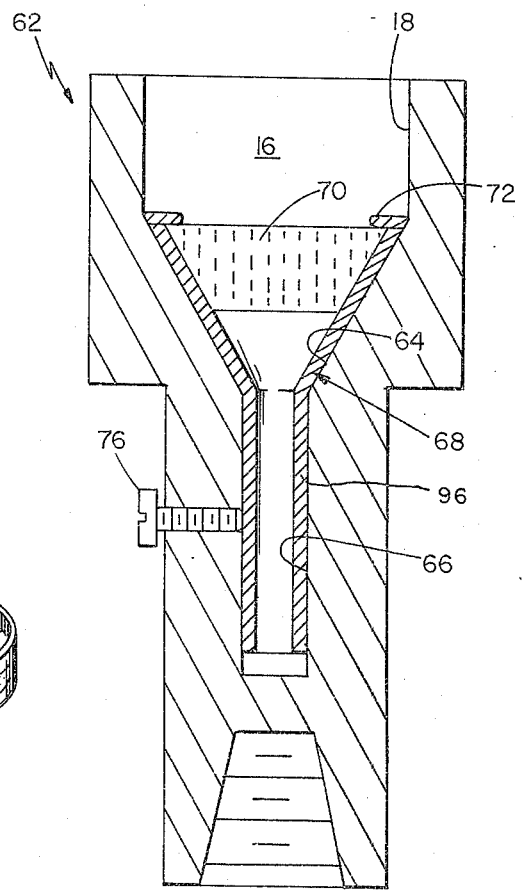
FIG. 6 is a cross section of a third embodiment of the invention with its filter in position.

FIG. 6 discloses still another embodiment of the invention wherein the structure 62 has a truncated conical filter mounting surface 64 and a bore 66 for receiving an interfitting filter holding housing 68. The filtering material 70 is mounted in housing 68 held in position by a solder bead 72. Crimp tabs have been used as an alternative filter securing means. The analyte, which is suspended in liquid 74, is collected by attaching a suction apparatus to the hollow shaft 96 of filter housing 68 and drawing the liquid through the filter 70 and housing 68 (FIG. 5). The analyte remains in or on the surface of the filter 70. To insure a quantitative transfer, a rinse may be used after liquid 74 has been removed and the filtering step may be repeated. When the analyte has been collected, the housing is set into the mounting surface 64 of structure 62. Set screw 76 holds it in position. This embodiment insures that analyte is present on the filter only and will not collect on the interior sheltering surface 18 of sheltered region 16.

Figure 3:
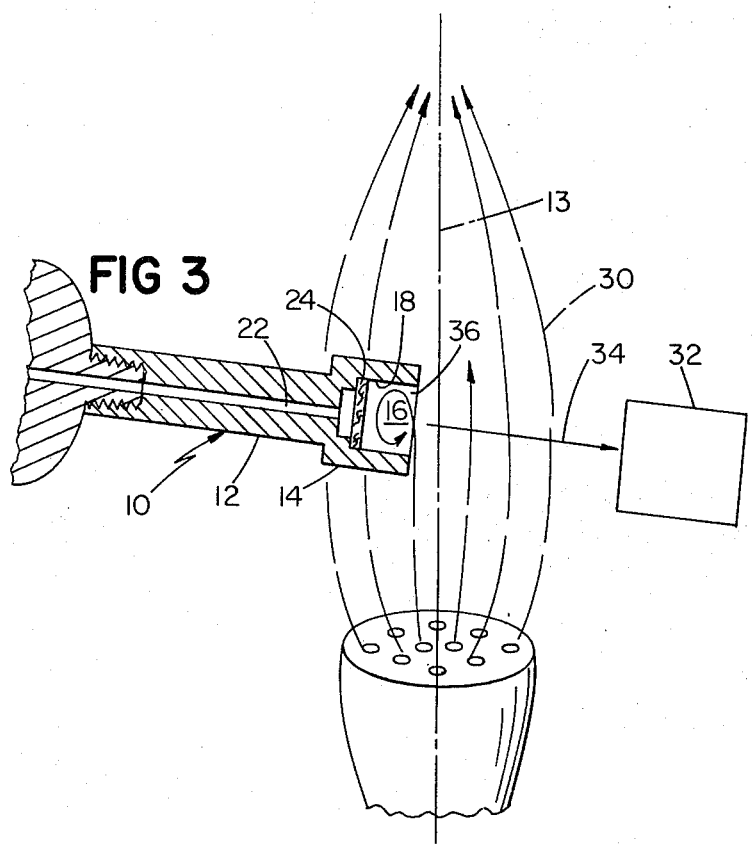
FIG. 3 is a cut away view of the structure of FIG. 1 positioned in a flame with analyte under analysis.

When the filtering is complete and the structure is assembled, analysis is accomplished by employing one of three optical detection means. Before detection, the analyte must be vaporized. The sheltered region serves to concentrate the vapor and allows its escape into the ambient environment only at a slow rate. Using one preferred detection means, the structure is placed within a flame 30 and a photometric analysis unit 32 is focused within the cavity. In FIG. 3, the structure 10 is shown positioned in the flame with the opening of the sheltered region 36 slightly pitched downwardly from a right angle relative to the axis 13 of the flame, the angle of tilt from normal ranging between about 5° and 20°, one preferred setting being 7°. The predominate direction of the flame, as indicated by flow lines, is across the opening; however, as schematically illustrated, the pitch of the holder causes some flame gas radicals to be intercepted.

As the head 14 is heated, the sample vaporizes and is exposed to the flame gas through the exposure path provided by the opening 36, while the volatilized sample itself is sheltered from being swept away by the structure defining sheltering surface 18. As mixing and interaction of the sample vapor and the flame gas occurs, molecular emission proceeds along optical path 34 to the detector of unit 32. The emission spectrum exhibits bands at frequencies characteristic of components of the sample as by reduction of sample molecules by hydrogen radicals or formation of new molecules by chemical interaction with the flame gases or other components within the cavity. Quantitative results may be obtained by the use of an intensity-time graph of the sample emissions, generated by a suitable recorder attached to the detector unit 32 as the emission promoting structure gradually heats after being inserted in the flame. The graph is then compared to calibration graphs generated in like manner with known amounts of the sample placed in the cavity.

In a second means of optical detection of analyte vapor, a source of high intensity light, such as a laser beam, is focused on the vapor within the cavity. Appropriate reflecting means is incorporated in the structure to reflect the beam out of the cavity, and characteristic fluorescence of components of the analyte is induced. In this detection method, detector unit 32 is adapted to measure the wavelengths of the fluorescing light produced, and the identity, and in some cases the quantity, of analyte present may be determined.

A third detection means within the scope of this invention comprises atomic or molecular absorption apparatus. A high intensity light generated by, e.g., a hollow cathode lamp, and having a wavelength which can be absorbed by a known species within the sheltered region, is focused on the analyte vapor within the cavity (i.e. Cadmium at 326 nm.). Reflecting means is appropriately situated to direct the light beam along optical path 34. Quantitative measurements are made by comparing the intensity of the entering light with the exiting light, the difference representing the degree of absorption taking place and hence an indirect measure of the amount of analyte present.

As an example of the technique herein described using the invention, selenium has been determined in selenium sulfide. In order to eliminate the interference effects arising from the varying volatilities of different selenium species, and from some other elements that interfere spectrally, a method of concentrating and purifying was employed. A measured amount of the sample was first reduced so that only elemental selenium was present. A fine glass-fiber filter, which quantitatively retains particles greater than 1 $\mu$m in diameter was inserted into the cavity and the sample passed through. After rinsing and drying, the emission detection technique was employed and the selenium emission was measured directly at 411 nm. The amount present was determined by reference to a calibration curve prepared by measuring emissions from known amounts of selenium. Interfering substances such as sulfer may be eliminated by this method and as little as 50 ngs of selenium may be determined.

Other embodiments are within the following claims.

What is claimed is:

1. In an emission promoting structure for use in an analyzer in conjunction with a flame and an optical emission analysis device, said structure defining a sheltered region for containing reactant, an exposure path for flame gas to interact with the reactant in the sheltered region and an optical path projecting out of said sheltered region whereby, under conditions influenced by said structure, reactant vapor in said sheltered region and flame gas can mix, interact and emit along said optical path to said analysis device radiation characteristic of said interaction, the improvement wherein said emission promoting structure is defined by a filter and sheltering wall means extending from said filter to an opening, said wall means sheltering said filter from said flame, and said opening and wall means defining said exposure path for gas from the flame to interact with reactant provided on said filter.

2. The apparatus of claim 1 having a filter mounting structure constructed to interfit with said wall means to position said filter in said wall-sheltered position, said mounting structure defining a fluid flow path for channeling fluid through said filter during collection prior to exposure to said gas.

3. The apparatus of claim 1 wherein said wall means defines a mounting structure to position said filter in said wall-sheltered position, said mounting structure defining a fluid flow path for channeling fluid through said filter during collection prior to exposure to said gas.

4. The apparatus of claim 1 wherein filter mounting structure of a first emission promoting structure defines a fluid flow path for channeling fluid through said filter during collection prior to exposure to said gas, said fluid flow path terminating in an exit port constructed to interfit with filter mounting structures of a second similar emission promoting structure carrying a filter of different characteristics.

* * * * *